United States Patent [19]

Glaser

[11] 4,059,103
[45] Nov. 22, 1977

[54] ABDOMINAL AND HERNIA SUPPORT

[76] Inventor: Ralph P. Glaser, 2709 Kirkwood Place, Hyattsville, Md. 20782

[21] Appl. No.: 692,216

[22] Filed: June 2, 1976

[51] Int. Cl.² .............................................. A61F 5/24
[52] U.S. Cl. ...................................... 128/96; 2/401; 128/98
[58] Field of Search ...................... 128/96, 98, 99, 100, 128/291, 105, 106, 158, 159, 518 R; 2/400, 401, 402, 403, 406

[56] References Cited

U.S. PATENT DOCUMENTS

| 792,424 | 6/1905 | King | 128/96 |
|---|---|---|---|
| 2,522,056 | 9/1950 | O'Brien | 128/96 |
| 2,593,262 | 4/1952 | Calabrese | 128/96 |
| 2,815,023 | 12/1957 | Hammersley | 128/99 |
| 3,097,641 | 7/1963 | Nelkin | 128/96 |
| 3,454,003 | 7/1969 | Kleber-Sailhen | 128/96 |

FOREIGN PATENT DOCUMENTS

| 1,177,805 | 4/1959 | France | 128/96 |
|---|---|---|---|
| 1,183,590 | 7/1959 | France | 128/291 |
| 119,699 | 10/1918 | United Kingdom | 128/100 |

Primary Examiner—John D. Yasko
Assistant Examiner—Michael H. Thaler

[57] ABSTRACT

This invention relates to a support intended primarily to prevent abdominal and/or inguinal hernias from bulging while the garment is worn. The garment consists of a one-piece, approximately I-shaped fabric with a front and rear area connected by a narrow neck portion passing through the crotch. Tension on the supporting fabric is provided by elastic bands which are stitched to the front and rear sections and pass over the hip. The garment, with a slight modification to accommodate anatomical differences, can equally serve males and females. The support comes in two styles basically of the same design and structure. One style is for one or two-sided hernias, and the other style is for one-sided hernias only. The left and right-sided supports are symmetrical opposites. An optional stiffener may be added to any style.

6 Claims, 4 Drawing Figures

ABDOMINAL AND HERNIA SUPPORT

SUMMARY OF THE INVENTION

My invention relates to abdominal and inguinal hernias. The object is to provide a simple, comfortable, firm yet yielding, efficient, inexpensive, easily adjustable and readjustable support for hernias in the abdominal and inguinal areas to be used by males and females allowing the wearer to indulge in vigorous movement, i.e., running, lifting, dancing, etc., with comfort.

A narrow neck section of the support passing through the crotch anchors the bottom part of the support firmly and comfortably while two elastic bands connecting the front and rear sections of the support passing over the hips provide a firm but yielding, uplifting support to the abdomen in general and the herniated areas. In addition, a heavier elastic band, attached at both ends only to the rear section of the support, passes across the front of the abdomen with the capability of being adjusted by placement over the part of the abdomen which needs support.

The support is mainly intended for small hernias, but that is not to say that larger hernias are outside the realm of its usefulness.

DETAILED DESCRIPTION

My invention is a one-piece garment which can be made from any firm, sturdy fabric. Thinner fabrics may be used in layers to build up the required firmness.

Figure 1:
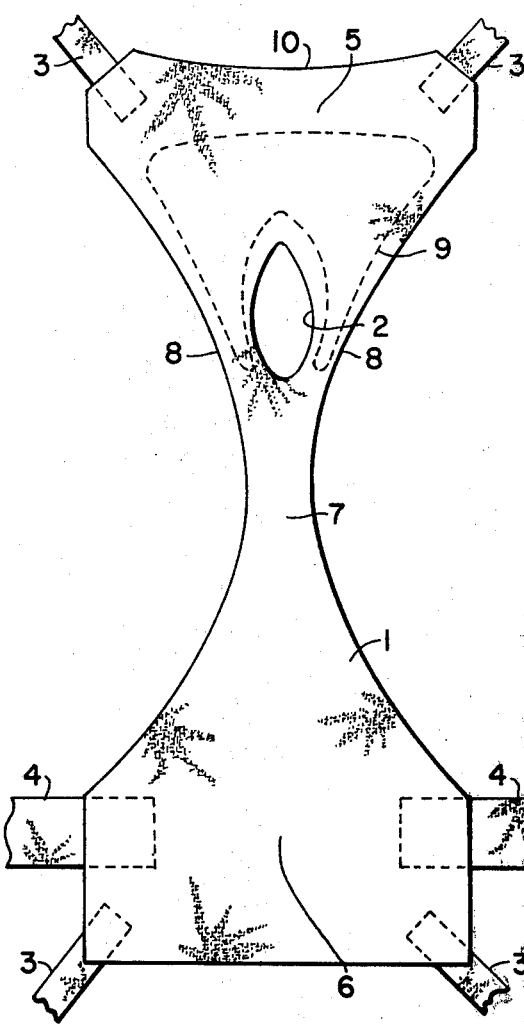
FIG. 1 is an inside view of the basic garment (male style) with elastic band connections.
Figure 3:
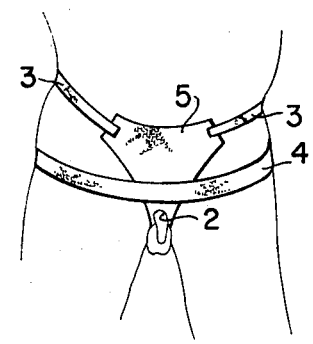
FIG. 3 is a front view of the basic garment as worn by a male.

The basic pattern is shown in FIG. 1. The numeral 1 indicates the fabric. The numeral 2 indicates an oval opening for the penis and scrotum. In garments for females 2 is omitted. Numeral 3 indicates a one-inch heavy duty elastic band which is stitched to the front 5 and rear 6 sections at an approximate 45° angle off horizontal. Two elastic bands 3 are used. Each band connects front 5 and rear 6 sections on each side, left and right, of the garment passing over the hip. Numeral 4 indicates a 2-inch wide, heavy duty, elastic band which extends from one side of the rear section 6 around the front of the abdomen (front section 5 when worn) to the other side of the rear section. The elastic band 4 is stitched horizontally to both sides of the rear section without any attachment to the front section.

Numeral 9 indicates an optional, flexible stiffener (i.e., a plastic sheath 20—30 thousanths of an inch thick). The stiffener would be inserted between two layers of fabric. In a garment for males, the stiffener 9 would be shaped and positioned as in FIG. 1 with a cut-out to accommodate the opening 2. In a garment for females, 2 being omitted, the stiffener would be positioned in the same manner but without the cut-out. A few stitches through the garment fabric layers and the stiffener holds the stiffener in place. The manufacturer could offer the stiffener as an extra piece with instructions on how to install it and the wearer could install it if more support were desired.

Numeral 7 indicates the crotch section.

Numeral 8 indicates the curved boundaries of the garment which approximate the curve of the groin.

The upper edge 10 of the front section 5 is slightly concave.

Figure 2:
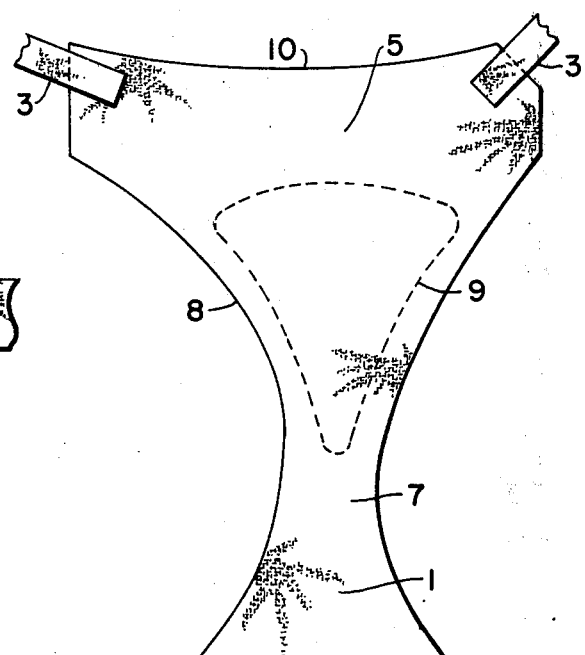
FIG. 2 is an outside view of the modified garment (for right-sided hernia) with elastic band connections.
Figure 4:
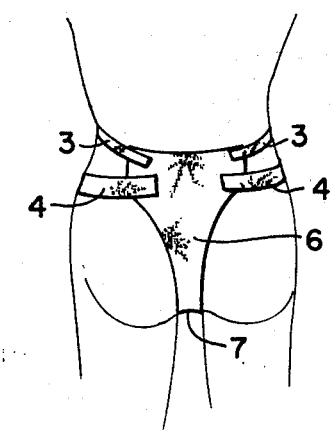
FIG. 4 is a rear view of the basic garment as worn by male or female.

The style represented by FIG. 1 is suitable for single or double hernias and abdominal support. The style represented by FIG. 2 is suitable for one-sided hernias and abdominal support in both males and females. The FIG. 2 style differs from the FIG. 1 style in that the crotch section 7 passes to the left or right side of the scrotum depending on the location of the hernia and that only one groin curve 8 is required (on the hernia side). Left and right hernia supports are the reversals of each other. The numerals in FIG. 2 have the same significances as in FIG. 1.

Various changes coming within the spirit of my invention may suggest themselves to those skilled in the art; hence I do not wish to be limited to the specific embodiments shown and described or uses mentioned, but intend the same to be merely exemplary, the scope of my invention being limited only by the appended claims.

What is claimed is:

1. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of a plurality of layers of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; a flat flexible stiffener inserted in said front section between said layers of fabric; said crotch section being laterally offset with respect to said front and rear sections so as to be adapted to pass to one side of a wearer's scrotum and said flexible stiffener being laterally offset in said front section to the same side as said lateral offset of said crotch section; whereby said support is used as a one-sided abdominal and hernia support and being adapted for use on either side of the wearer by reversing said support so that the left and right sides of said front section exchange places and the left and right sides of said rear section exchange places.

2. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of at least one layer of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; said crotch section being laterally offset with respect to said front and rear sections so as to be adapted to pass to one side of a wearer's scrotum; whereby said support is used as a one-sided, unstiffened abdominal and hernia support and being adapted for use on either side of the wearer by reversing said support so that the left and right sides of said front section exchange places and the left and right sides of said rear section exchange places.

3. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of a plurality of layers of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; a flat flexible stiffener inserted in said front section between said layers of fabric; said crotch section being centrally set with respect to said front and rear sections; said front section being adapted for male wearers by means of an opening to allow passage of the wearer's penis and scrotum, and said flexible stiffener being centrally placed in said front section; whereby said support is used as a two-sided abdominal and hernia support for males.

4. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of at least one layer of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; said crotch section being centrally set with respect to said front and rear sections; said front section being adapted for male wearers by means of an opening to allow passage of the wearer's penis and scrotum; whereby said support is used as a two-sided unstiffened abdominal and hernia support for males.

5. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of a plurality of layers of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; a flat flexible stiffener inserted in said front section between said layers of fabric; said crotch section being centrally set with respect to said front and rear sections and said flexible stiffener being centrally placed in said front section; whereby said support is used as a two-sided abdominal and hernia support for females.

6. An abdominal and hernia support comprising a crotch section shaped so as to be adapted to fit next to a wearer's crotch; a front section having left and right sides and shaped so as to be adapted to fit next to a wearer's abdomen; a rear section having left and right sides and shaped so as to be adapted to fit next to a wearer's buttocks; said crotch, front and rear sections being continuous and being constructed of at least one layer of non-elastic fabric; a first elastic band stitched to the left side of the front section and the left side of the rear section and adapted to rest above the left hip of a wearer; a second elastic band stitched to the right side of the front section and the right side of the rear section and adapted to rest above the right hip of a wearer; a third elastic band stitched to the left and right sides of said rear section and adapted for passing around said front section without attachment thereto; said crotch section being centrally set with respect to said front and rear sections; whereby said support is used as a two-sided, unstiffened abdominal and hernia support for females.

* * * * *